United States Patent
Savonnet et al.

(10) Patent No.: US 9,096,617 B2
(45) Date of Patent: Aug. 4, 2015

(54) CAU-1-N3 ORGANIC-INORGANIC HYBRID SOLID, EQUIPPED WITH AN AZIDE GROUP, AND PROCESS FOR ITS PREPARATION

(75) Inventors: Marie Savonnet, Lyons (FR); David Farrusseng, Belmont d'Azegues (FR); Catherine Pinel, Lyons (FR); Delphine Bazer-Bachi, Irigny (FR); Nicolas Bats, Saint Symphorien d'Ozon (FR); Vincent Lecocq, Orlienas (FR)

(73) Assignees: CNRS, Paris Cedex (FR); IFP ENERGIES NOUVELLES, Rueil-Malmaison Cedex (FR)

( * ) Notice: Subject to any disclaimer, the term of this patent is extended or adjusted under 35 U.S.C. 154(b) by 587 days.

(21) Appl. No.: 13/503,468

(22) PCT Filed: Oct. 6, 2010

(86) PCT No.: PCT/FR2010/000670
§ 371 (c)(1),
(2), (4) Date: Jul. 23, 2012

(87) PCT Pub. No.: WO2011/048282
PCT Pub. Date: Apr. 28, 2011

(65) Prior Publication Data
US 2012/0296104 A1    Nov. 22, 2012

(30) Foreign Application Priority Data
Oct. 23, 2009 (FR) ...................... 09 05103

(51) Int. Cl.
C07F 5/06 (2006.01)

(52) U.S. Cl.
CPC ...................... *C07F 5/069* (2013.01)

(58) Field of Classification Search
CPC ........................................... C07F 5/069
See application file for complete search history.

(56) References Cited

PUBLICATIONS

Zaragoza Dorwald, Side Reactions in Organic Synthesis, 2005, WILEY-VCH Verlag GmbH & Co. KGaA, Weinheim, Preface. p. IX.*
Wang et al, Inorganic Chemistry, Accessing Postsynthetic Modification in a Series of Metal-Organic Frameworks and the Influence of Framework Topology on Reactivity, 2009, 48(1, pp. 296-306.*
International Search Report of PCT/FR2010/000670 (Jan. 14, 2011).
M. Savonnet et al., "Generic Postfunctionalization Route from Amino-Derived Metal-Organic Frameworks", Journal of the American Chemical Society, vol. 132, No. 13 (Apr. 7, 2010) pp. 4518-4519.
Z. Wang et al., "Accessing Postsynthetic Modification in a Series of Metal-Organic Frameworks and the Influence of Framework Topology on Reactivity", Inorganic Chemistry, vol. 48, No. 1 (2009) pp. 296-306.
T. Ahnfeldt et al., "[Al4(OH)2(OCH3)4(H2N-bdc)3]xH20: A 12-Connected Porous Metal-Organic Framework with an Unprecedented Aluminum-Containing Brick", Angewandte Chemie, International Edition, vol. 48, No. 28 (Jun. 29, 2009) pp. 5163-5166.

* cited by examiner

*Primary Examiner* — Paul A Zucker
(74) *Attorney, Agent, or Firm* — Millen, White, Zelano & Branigan, P.C.

(57) ABSTRACT

The invention describes a crystallized hybrid solid with an organic-inorganic matrix, of a three-dimensional structure, containing an inorganic network of aluminum-based metal centers that are connected to one another by organic ligands that consist of the entity —$O_2C$—$C_6H_3$—$N_3$—$CO_2$—. Said solid is called CAU-1-$N_3$ and has an X-ray diffraction diagram as given below.

11 Claims, 1 Drawing Sheet

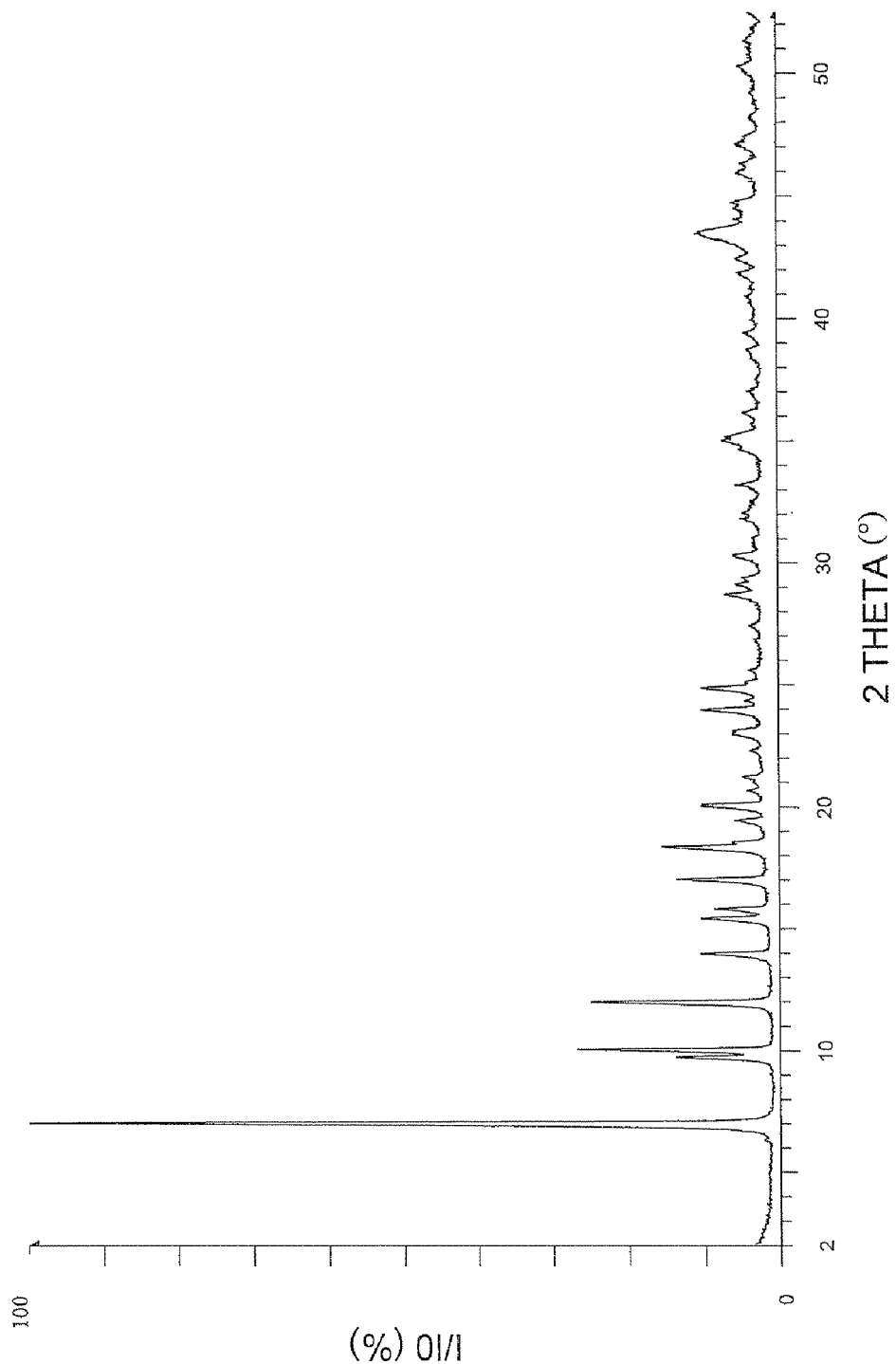

CAU-1-N3 ORGANIC-INORGANIC HYBRID SOLID, EQUIPPED WITH AN AZIDE GROUP, AND PROCESS FOR ITS PREPARATION

TECHNICAL FIELD OF THE INVENTION

This invention relates to a new crystallized hybrid solid with an organic-inorganic matrix, of a three-dimensional structure, and to the process for its preparation starting from the crystallized hybrid solid with a CAU-1 organic-inorganic matrix that is already described in the literature. Said new solid, object of this invention, carries an azide group and is called CAU-1-$N_3$ in the description below. Said CAU-1-$N_3$ solid has a crystalline structure that is identical to the one of the CAU-1 solid from which it is obtained by a post-synthesis functionalization method. Said CAU-1-$N_3$ solid is advantageously used in applications as a catalyst or adsorbent or else as an intermediate compound for obtaining functionalized crystallized hybrid solids with an organic-inorganic matrix.

STATE OF THE ART

The modification of materials by functionalization is a stage that is often necessary for the development of solids that have suitable properties for a given application. Actually, it may be desirable to improve the physico-chemical properties of a material, by modifying its surface, for example, so that the new properties that are obtained after modifications are more suitable for separation or catalysis applications.

One of the means that is commonly used to modify the surface of a material consists in reacting the functional groups that are initially present on its surface by entities that have the desired groups for the application being considered. The groups that are present on the surface of a material can be hydroxyl groups (—OH) or any other group (amino-$NH_2$ or —NH—, for example) that it is desired to modify so as to orient the chemical reactivity of the surface of the material. The reagents that are used will have the necessary functionalities for reacting with the groups that are initially present on the surface of the material, and the result of the reaction will be a new chemical group that has the desired reactivity. One example of such a transformation consists in reacting the hydroxyl groups of the surface of a silica by a silane that carries an amine group (D. Brunel, *Microporous and Mesoporous Materials*, 1999, 27, 329-344). Thus, the hydroxyl group is transformed into an amine group that is better able to catalyze basic reactions or to collect $CO_2$, for example. This methodology can be applied to any material that initially has reactive groups. These materials can be oxides, zeolites, or else organic/inorganic hybrid materials, also called coordination polymers.

These coordination polymers, of which the first were described in the 1960's, are the object of a growing number of publications. Actually, the effervescence around these materials made it possible to attain an advanced structural diversity in little time (Férey, G., l'actualité chimique [Chemical Issues], January 2007, No. 304). Conceptually, the porous hybrid solids with an organic-inorganic mixed matrix are quite similar to porous solids with an inorganic skeleton Like the latter, they combine chemical entities by giving rise to a porosity. The primary difference resides in the nature of these entities. This difference is particularly advantageous and is at the origin of the entire versatility of this category of hybrid solids. Actually, the size of the pores becomes, by using organic ligands, adjustable by means of the length of the carbon-containing chain of said organic ligands. The framework, which, in the case of inorganic porous materials, can accept only some elements (Si, Al, Ge, Ga, and optionally Zn), can, in this case, collect all of the cations except for the alkalines. For the preparation of these hybrid materials, no specific structuring agent is required; the solvent provides this effect by itself.

It therefore clearly appears that this family of hybrid materials makes possible a multiplicity of structures and consequently comprises solids that are finely adapted to the applications for which they are designed.

The coordination polymers comprise at least two elements that are called connectors and ligands whose orientation and number of connecting sites are decisive in the structure of the hybrid material. From the diversity of these ligands and connectors, an immense variety of hybrid materials is born, as has already been specified.

Ligand is defined as the organic part of the hybrid material. These ligands are most often di- or tricarboxylates or derivatives of pyridine. Some commonly encountered organic ligands are shown below: bdc=benzene-1,4-dicarboxylate, btc=benzene-1,3,5-tricarboxylate, ndc=naphthalene-2,6-dicarboxylate, bpy=4,4'-bipyridine, hfipbb=4,4'-(hexafluoroisopropylidene)-bisbenzoate, cyclam=1,4,8,11-tetraazacyclotetradecane.

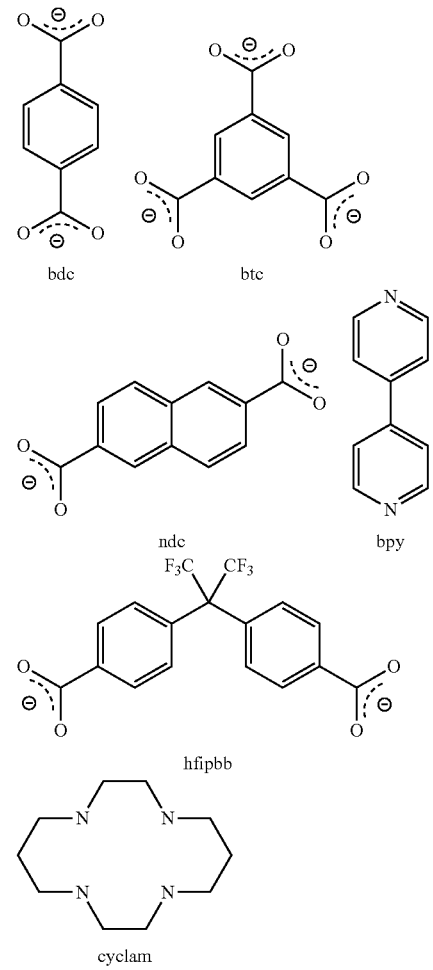

Connector is defined as the inorganic entity of the hybrid material. It may be a cation by itself, a dimer, trimer or tetramer, or else a chain or a plane.

Within the framework of this invention, the ligand that is used for the preparation of the solid according to the invention is 2-amino-terephthalic acid. For its part, the inorganic entity that plays the role of connector is aluminum.

The teams of Yaghi and Férey have thus described a large number of new hybrid materials (series of MOF—"Metal Organic Framework"—and series of MIL—"Materiaux de l'Institut Lavoisier [Lavoisier Institute Materials]"—respectively). Numerous other teams have followed this path, and today, the number of new hybrid materials described is expanding rapidly. Most often, the purpose of the studies is to develop ordered structures, having extremely large pore volumes, good thermal stability, and adjustable chemical functionalities.

For example, Yaghi et al. describe a series of boron-based structures in the patent application US 2006/0154807 and indicate their advantage in the field of gas storage. The patent U.S. Pat. No. 7,202,385 discloses a particularly complete summary of the structures that are described in the literature and perfectly illustrates the multitude of materials already existing today.

The preparation of organic-inorganic hybrid materials that have a reactive organic group (grafted MOF) can be implemented by two primary paths: functionalization by self-assembly and functionalization by post-modification. The functionalization by self-assembly is implemented by bringing an organic ligand that has the desired reactive group (graft) into the presence of an inorganic compound that has the role of connector. This functionalization method is often difficult to implement because of problems linked to the solubilization and the reactivity of the functionalized ligands. In particular, the ligands that carry an —OH, —COOH or —NH$_2$ group run the risk of interacting with the inorganic compound (connector) that then leads to non-isostructural solids with non-grafted reference MOF. The functionalization by post-modification is an advantageous alternative method that does not have limits of functionalization by self-assembly. The functionalization by post-modification consists in directly modifying the organic group of at least one type of ligand that is present in the MOF by a chemical reaction (grafting), more specifically in replacing the initial organic group by an organic group whose reactivity is preferred for a subsequent application. This method suggests the presence on the initial MOF of an organic group that is accessible and reactive for grafting. In the literature, the organic-inorganic hybrid materials that carry a ligand with an —NH$_2$ amino group such as DMOF-1—NH$_2$ (Z. Q. Wang; K. K. Tanabe, S. M. Cohen, *Inorganic Chemistry*, 2009, 48, 296-306) are described as good substrates for the grafting of numerous groups, in particular aldehydes, isocyanates, and acid anhydrides.

DESCRIPTION OF THE INVENTION

This invention has as its object a new crystallized hybrid solid with an organic-inorganic matrix that has a three-dimensional structure. This new solid is called CAU-1-N$_3$. It contains an inorganic network of aluminum-based metal centers that are connected to one another by organic ligands that consist of the entity —O$_2$C—C$_6$H$_3$—N$_3$—CO$_2$— (N$_3$-bdc ligand).

The CAU-1-N$_3$ crystallized hybrid solid according to the invention has an X-ray diffraction diagram that includes at least the lines that are recorded in Table 1. This diffraction diagram is obtained by radiocrystallographic analysis by means of a diffractometer by using the conventional method of powders with the Kα1 radiation of copper (λ=1.5406 Å). Starting from the position of diffraction peaks shown by the angle 2θ, the reticular equidistances $d_{hkl}$ that are characteristic of the sample are calculated by applying Bragg's equation. The measuring error $\Delta(d_{hkl})$ to $d_{hkl}$ is calculated using Bragg's equation based on the absolute error $\Delta(2\theta)$ that is assigned to the measurement of 2θ. An absolute error of $\Delta(2\theta)$ that is equal to ±0.02° is commonly allowed. The relative intensity $I/I_o$ assigned to each value of $d_{hkl}$ is measured according to the height of the corresponding diffraction peak. The X-ray diffraction diagram of the CAU-1-N$_3$ crystallized hybrid solid according to the invention comprises at least the lines with the values of $d_{hkl}$ given in Table 1. In the column of $d_{hu}$, the mean values for the interrectical distances are indicated in angstroms (Å). Each of these values is to be assigned the measuring error $\Delta(d_{hkl})$ of between ±0.3 Å and ±0.01 Å.

TABLE 1

Mean Values for $d_{hkl}$ and Relative Intensities Measured on an X-Ray Diffraction Diagram of the CAU-1-N$_3$ Crystallized Hybrid Solid.

| 2 Theta (°) | $d_{hkl}$ (Å) | $I/I_o$ |
| --- | --- | --- |
| 6.93 | 12.74 | FF |
| 9.68 | 9.13 | ff |
| 9.98 | 8.85 | f |
| 11.94 | 7.41 | f |
| 13.92 | 6.36 | ff |
| 15.37 | 5.76 | ff |
| 15.76 | 5.62 | ff |
| 16.97 | 5.22 | ff |
| 18.30 | 4.84 | ff |
| 19.41 | 4.57 | ff |
| 20.03 | 4.43 | ff |
| 20.64 | 4.30 | ff |
| 21.19 | 4.19 | ff |
| 22.30 | 3.98 | ff |
| 23.02 | 3.86 | ff |
| 23.95 | 3.71 | ff |
| 24.34 | 3.65 | ff |
| 24.84 | 3.58 | ff |
| 25.57 | 3.48 | ff |
| 26.78 | 3.33 | ff |
| 27.41 | 3.25 | ff |
| 28.70 | 3.11 | ff |
| 29.11 | 3.06 | ff |
| 29.38 | 3.04 | ff |
| 30.30 | 2.95 | ff |
| 30.98 | 2.88 | ff |
| 31.81 | 2.81 | ff |
| 32.08 | 2.79 | ff |
| 32.52 | 2.75 | ff |
| 33.23 | 2.69 | ff |
| 34.69 | 2.58 | ff |
| 35.01 | 2.56 | ff |
| 36.15 | 2.48 | ff |
| 37.04 | 2.42 | ff |
| 37.54 | 2.39 | ff |
| 38.50 | 2.34 | ff |
| 38.73 | 2.32 | ff |
| 39.42 | 2.28 | ff |
| 39.98 | 2.25 | ff |
| 40.93 | 2.20 | ff |
| 41.89 | 2.16 | ff |
| 42.49 | 2.13 | ff |
| 43.54 | 2.08 | ff |
| 44.56 | 2.03 | ff |
| 44.77 | 2.02 | ff |
| 46.00 | 1.97 | ff |
| 46.34 | 1.96 | ff |
| 47.15 | 1.93 | ff |
| 47.42 | 1.92 | ff |
| 48.29 | 1.88 | ff |
| 49.26 | 1.85 | ff |
| 50.10 | 1.82 | ff |

TABLE 1-continued

Mean Values for $d_{hkl}$ and Relative Intensities Measured on an X-Ray Diffraction Diagram of the CAU-1-N$_3$ Crystallized Hybrid Solid.

| 2 Theta (°) | $d_{hkl}$ (Å) | I/I$_o$ |
|---|---|---|
| 50.32 | 1.81 | ff |
| 51.41 | 1.78 | ff |
| 51.87 | 1.76 | ff | where
FF = Very High;
F = High;
m = Medium;
mf = Medium Low;
f = Low; and
ff = Very Low.
The relative intensity I/I$_o$ is provided in relation to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85.

BRIEF DESCRIPTION OF THE DRAWING

The CAU-1-N$_3$ crystallized hybrid solid according to the invention has a crystalline structure with a base or topology that is characterized by its X-diffraction diagram provided by FIG. 1. The crystalline structure of the CAU-1-N$_3$ crystallized hybrid solid according to the invention is identical to the one that is exhibited by the CAU-1 crystallized hybrid solid that is described in the literature (T. Ahnfeldt, N. Guillou, D. Gunzelmann, I. Margiolaki, T. Loiseau, G. Ferey, J. Senker, N. Stock, *Angew. Chem. Int. Ed,* 2009, Vol. 48, Issue 28, 5163-5166) and from which said CAU-1-N$_3$ solid is obtained, in accordance with the process for preparation described farther down in this description.

The CAU-1-N$_3$ crystallized hybrid solid according to the invention has a three-dimensional structure in which the inorganic network—formed by Al$^{3+}$-cation-based metal centers that perform the role of connectors—is linked together by deprotonated terephthalic ligands (—O$_2$C—C$_6$H$_3$—N$_3$—CO$_2$—) that carry an N$_3$ azide group on the aromatic cycle. An essential characteristic of the CAU-1-N$_3$ crystallized hybrid solid according to the invention resides in the presence of the azide group on the aromatic cycle of each of the deprotonated terephthalic ligands, more specifically called 2-azido-terephthalate ligands (denoted N$_3$-bdc). The structure that is obtained, identical to the one of the CAU-1 solid, is a three-dimensional structure, in which wheel-shaped bricks of [Al$_8$(OH)$_4$(OCH$_3$)$_8$]$^{12+}$ are linked to one another by 12 deprotonated terephthalic ligands (—O$_2$C—C$_6$H$_3$—N$_3$—CO$_2$—). Each aluminum atom is hexa-coordinated: each aluminum atom is surrounded by three oxygen atoms that are obtained from three deprotonated terephthalic ligands (N$_3$-bdc ligand), an oxygen atom from hydroxyl groups, and two oxygen atoms from the methoxyl groups. Thus, the structure of the CAU-1-N$_3$ solid has deformed octahedral and tetrahedral cages. The CAU-1-N$_3$ crystallized hybrid solid according to the invention thus has a chemical composition that has Al$_4$(OH)$_2$(OCH$_3$)$_4$ (N$_3$-bdc)$_3$ for its base pattern. This pattern is repeated n times, with the value of n based on the crystallinity of said solid.

The CAU-1-N$_3$ crystallized hybrid solid according to the invention has also been characterized by Fourier Transform Infrared (FT-IR) spectroscopy and by $^1$H NMR in such a way as to verify the presence of the azide group on each of the terephthalate ligands. Thus, the spectrum that is obtained by FT-IR has a characteristic band of the azide group at 2,124 cm$^{-1}$. The $^1$H-NMR analysis is implemented on a sample of said CAU-1-N$_3$ hybrid solid according to the invention, after digestion and total dissolution of said sample in a DC1/D$_2$O/DMSO-d$_6$ deuterated mixture according to an operating mode described in the literature (Z. Q. Wang, S. M. Cohen, *Journal of the American Chemical Society,* 2007, 129, 12368-12369). Coupled to the FT-IR analysis, the $^1$H-NMR analysis confirms the presence of the N$_3$ azide group on the aromatic cycle of the deprotonated terephthalic ligand: δ=7.73-7.83 ppm, m, 3H, ArH. The 3 protons leading to the detection of the multiplet correspond to the 3 protons carried by the aromatic cycle of the 2-azido-terephthalate (N$_3$-bdc) ligand.

This invention also has as its object a process for the preparation of the CAU-1-N$_3$ crystallized hybrid solid. Said CAU-1-N$_3$ solid is prepared from the CAU-1 crystallized hybrid solid that is described in the literature (T. Ahnfeldt, N. Guillou, D. Gunzelmann, I. Margiolaki, T. Loiseau, G. Ferey, J. Senker, N. Stock, *Angew. Chem. Int. Ed,* 2009, Vol. 48, Issue 28, 5163-5166). Said CAU-1 solid has a three-dimensional structure, in which wheel-shaped bricks of [Al$_8$(OH)$_4$(OCH$_3$)$_8$]$^{12+}$ are linked to one another by 12 2-aminoterephthalate ligands that carry an —NH$_2$ amine group on the aromatic cycle (—O$_2$C—C$_6$H$_3$—NH$_2$—CO$_2$—, NH$_2$-bdc ligand). Each aluminum atom is hexa-coordinated and is surrounded by three oxygen atoms that are obtained from three 2-aminoterephthalate ligands, an oxygen atom from hydroxyl groups, and two oxygen atoms from methoxyl groups. Thus, the structure of the CAU-1 solid has deformed octahedral and tetrahedral cages. The CAU-1 crystallized hybrid solid thus has a chemical composition that has Al$_4$(OH)$_2$(OCH$_3$)$_4$ (N$_2$-bdc)$_3$ for its base pattern. This pattern is repeated n times, with the value of n based on the crystallinity of said solid.

A method for preparation of said CAU-1 solid is described in the literature (T. Ahnfeldt, N. Guillou, D. Gunzelmann, I. Margiolaki, T. Loiseau, G. Ferey, J. Senker, N. Stock, *Angew. Chem. Int. Ed,* 2009, Vol. 48, Issue 28, 5163-5166). The process for preparation of the invention makes possible the replacement of the —NH$_2$ amine group that is present in the CAU-1 solid by the N$_3$ azide group. The process for preparation according to the invention comprises at least the following stages:

i/ Introduction, into a polar solvent S, of at least said CAU-1 crystallized hybrid solid, at least one organic compound Q that contains an N$_3$ azide group, and at least one intermediate reagent R that contains an NO$_2$ nitrite group in a proportion such that the reaction mixture has the following molar composition, based on a molar equivalent of the —NH$_2$ group that is present in the CAU-1 solid:

1CAU-1:1-40R:1-30Q:100-400S ii/ Reaction of said reaction mixture at a temperature of between 0 and 100° C. for a period of between 1 and 24 hours to obtain said CAU-1-N$_3$ crystallized hybrid solid, iii/ Filtration, and then washing of said CAU-1-N$_3$ crystallized hybrid solid, iv/ Drying of said CAU-1-N$_3$ crystallized hybrid solid.

In accordance with said stage i) of said process for the preparation of the CAU-1-N$_3$ crystallized hybrid solid according to the invention, said CAU-1 crystallized hybrid solid is dried in advance before being introduced into said polar solvent. The drying of said CAU-1 crystallized hybrid solid is advantageously implemented at a temperature of between 20 and 100° C. for a period of between 1 and 24 hours, very advantageously for a period of approximately 12 hours. The drying is done in air or under vacuum, in a preferred manner under vacuum.

In accordance with said stage i) of the process for preparation according to the invention, said organic compound Q that contains an N$_3$ azide group is advantageously selected from among trimethylsilyl azide (TMS-$N_3$, $(CH_3)_3SiN_3$), triflyl azide (Tf$N_3$, where Tf=$CF_3SO_2$), p-tosyl azide (Ts$N_3$ or 4-methylbenzenesulfonyl azide of formula $C_6H_4(CH_3)SO_2N_3$), and sodium azide (Na$N_3$). In a preferred manner, said organic compound Q that contains an $N_3$ group is trimethylsilyl azide (TMS-$N_3$).

In accordance with said stage i) of the process for preparation according to the invention, said intermediate reagent R that contains an $NO_2$ nitrite group is advantageously selected from among alkaline reagents such as sodium nitrite (Na$NO_2$) and calcium nitrite (Ca($NO_2$)$_2$), metal reagents, and alkoyl-type reagents such as tert-butyl-nitrite (tBuONO, $(CH_3)_3$CONO). In a very preferred manner, said intermediate reagent R that contains an $NO_2$ nitrite group is tert-butyl-nitrite (tBuONO). Said intermediate reagent R that contains an $NO_2$ nitrite group ensures the formation of a diazonium salt that next reacts with the organic compound Q.

The polar solvent S that is used in said stage i) of the process for preparation according to the invention is preferably volatile. It is very advantageously selected from among tetrahydrofuran (THF) and acetonitrile.

In accordance with said stage i) of the process for preparation according to the invention, the reaction mixture preferably has the following molar composition, based on a molar equivalent of the —$NH_2$ group that is present in the CAU-1 solid:

1CAU-1:10-30R:10-20Q:100-200S

Said reaction stage in accordance with said stage ii) of the process for preparation according to the invention is preferably implemented at a temperature of between 0 and 60° C., and even more preferably at ambient temperature. The reaction mixture is stirred using a magnetic stirrer. The reaction period is between 1 and 24 hours, preferably between 5 and 15 hours, and most often approximately 12 hours. The solid that is obtained at the end of said stage ii) is a CAU-1-$N_3$ crystallized hybrid solid that has an X-ray diffraction diagram that includes at least the lines that are recorded in Table 1.

In accordance with said stage iii) of the process for preparation according to the invention, said CAU-1-$N_3$ crystallized hybrid solid that is obtained at the end of said stage ii) is filtered and then washed with suitable solvents. The washing of said CAU-1-$N_3$ solid is preferably implemented by a first washing sequence by means of polar solvents, for example THF, followed by a second washing sequence by means of volatile solvents, for example dichloromethane. The washing stage of said CAU-1-$N_3$ crystallized hybrid solid is initiated, for example, by implementing 3 sequences of washing with THF followed by 3 sequences of washing with $CH_2Cl_2$ dichloromethane.

In accordance with said stage iv) of the process for preparation according to the invention, said CAU-1-$N_3$ crystallized hybrid solid is dried. The drying is done in air or under vacuum at between 20° C. and 100° C., preferably at ambient temperature, for a period that varies between 1 and 24 hours. In a preferred manner, the drying is done at ambient temperature under vacuum for a period that varies between 1 and 24 hours, most often approximately 12 hours.

The solid that is obtained at the end of stage iv) is identified as being the CAU-1-$N_3$ crystallized hybrid solid according to the invention. The analyses that are implemented on the solid that is obtained at the end of the process for preparation according to the invention demonstrate the effectiveness of the treatment by post-modification. In particular, the analysis that is implemented on the CAU-1-$N_3$ crystallized hybrid solid by XRD demonstrates that the treatment of functionalization by post-modification that makes it possible to replace the —$NH_2$ amino group by the —$N_3$ azide group does not affect the structure and the crystallinity of the solid. The FT-IR analysis reveals the presence of the —$N_3$ azide group on each of the deprotonated terephthalic ligands in the CAU-1-$N_3$ solid. Coupled to the FT-IR analysis, the $^1$H-NMR analysis confirms the presence of the —$N_3$ azide group on each of the deprotonated terephthalic ligands in the CAU-1-$N_3$ solid and makes it possible to estimate the rate of modification of the amino groups into $N_3$ azide groups. In accordance with the process for preparation according to the invention, this rate of modification is very high, i.e., at least equal to 95%, and preferably at least equal to 98%. The rate of modification is calculated by quantifying the decrease in the relative area of the signals of aromatic protons of the CAU-1 form relative to those of the CAU-1-$N_3$ form. The $^1$H-NMR spectrum of the CAU-1-$N_3$ solid according to the invention has new signals that are linked to the appearance of an integral multiplet for 3 protons, which correspond to the 3 protons that are carried by the aromatic cycle of the 2-azido-terephthalate ($N_3$-bdc) ligand.

EXAMPLES

The CAU-1 and CAU-1-$N_3$ crystallized hybrid solids that are obtained at the end of the implementation of the preparation protocols illustrated by the following Examples 1 and 2 have been analyzed by X-ray diffraction, by Fourier Transform Infrared (FT-IR) spectroscopy, and by nuclear magnetic resonance of hydrogen ($^1$H NMR).

The X-ray diffraction diagrams are obtained by radiocrystallographic analysis by using the conventional powder method by means of a Bruker D5005 diffractometer (CuK$\alpha_{1+2}$=0.15418 nm) that is equipped with a graphite curved rear monochromator and a scintillation detector. The analyses of the solids have been recorded with the Debye-Scherrer method from 3 to 80° (2θ) with a pitch of 0.02° for 8 seconds.

The infrared analyses are done using KBr pellets on a Bruker Vector 22 FT-IR device with a useful operating range of: 4,000-400 $cm^{-1}$.

The nuclear magnetic resonance spectra in solution are obtained using a Bruker Avance 250 NMR spectrometer (5.87 T, 250 MHz for $^1$H).

Example 1

Preparation of the CAU-1 Crystallized Hybrid Solid 365.3 mg of hydrated aluminum chloride (AlCl$_3$.6H$_2$O, 1.5 mmol, Aldrich, 98%) is placed in a PTFE receptacle with an inside volume of 40 ml, and 94 mg of 2-aminoterephthalic acid (NH$_2$—H$_2$-bdc, 0.5 mmol, Alfa Aesar, 99%) and 10 ml of methanol (ACROS ORGANICS, 99.99%) are added thereto. The mixture is stirred for 5 minutes using a magnetic stirring mechanism. The PTFE receptacle is then transferred into an autoclave and then heated without being stirred at 125° C. for 5 days. After cooling and filtration, the crystallized solid that is obtained is washed with methanol (Acros Organics, 99.99%) and then with a hot solution (24 hours, 160° C.) of DMF (Aldrich, 99.8%), and is impregnated (48 hours) in dichloromethane (ACROS ORGANICS, 99.99%). After drying in the oven (air) at a temperature that is equal to 120° C. for a period of 12 hours, a material in the form of powder that consists of CAU-1 crystals is obtained.

Said CAU-1 crystallized hybrid solid is analyzed by X-ray diffraction, by Fourier Transform Infrared spectroscopy, and by nuclear magnetic resonance of hydrogen ($^1$H NMR).

The X-ray diffraction analysis reveals that said solid that is obtained in Example 1 is identified as consisting of CAU-1 solid: the diffractogram that is carried out on said solid is identical to the one that is presented in *Angew. Chem. Int. Ed,* 2009, Vol. 48, Issue 28, 5163-5166.

The FT-IR analysis reveals the presence of the —$NH_2$ amino group in the CAU-1 solid.

IR (KBr pellet), ν ($cm^{-1}$): 3454, 3386, 2935, 1669, 1574, 1432, 1393, 1260, 1066, 788, 607, 547. The bands at 3,454 and 3,386 $cm^{-1}$ are attributed to the amine group.

The $^1$H-NMR analysis is implemented on a sample of the CAU-1 solid after digestion and total dissolution of the sample in a DCl/$D_2O$/DMSO-$d_6$ deuterated mixture according to the operating mode that is described in the literature (Z. Q. Wang, S. M. Cohen, *Journal of the American Society,* 2007, 129, 12368-12369): 10 mg of CAU-1 hybrid solid is digested and dissolved in 1.5 ml of deuterated DMSO and 0.2 ml of a dilute DCl solution (prepared from a solution that contains 0.23 ml of DCl/$D_2O$ at 35% and 1 ml of deuterated DMSO).

Coupled to the FT-IR analysis, the $^1$H-NMR analysis also reveals the presence of the —$NH_2$ amino group in the CAU-1 solid. $^1$H NMR, 250 MHz, t.a, δ (ppm/(DCl/$D_2O$/DMSO-$d_6$)): 6.68 (d, 1H, J=8 Hz); 7.03 (s, 1H); 7.6 (d, 1H, J=8 Hz).

Example 2

Preparation of the CAU-1-$N_3$ Solid b
Post-Modification of the CAU-1 Hybrid Solid 80 mg (0.3 mmol equivalent of —$NH_2$) of CAU-1 solid, obtained at the end of the process that is illustrated in Example 1, is vacuum-dried at 85° C. for 12 hours and then placed in a pill machine (8 ml capacity) with 3 ml (37 mmol) of THF, 0.74 ml (6.32 mmol, 21 eq) of tBuONO (Aldrich, 90%), and 0.65 ml (5 mmol, 17 eq) of TMS-$N_3$ (Aldrich, 95%). After 12 hours of reaction at ambient temperature, the solid is filtered and then washed three times with 8 ml of THF (Carlo Erba, 99.5%), and then three times with 8 ml of $CH_2Cl_2$ (ACROS ORGANICS, 99.99%) before being vacuum-dried at ambient temperature for 12 hours.

The solid that is obtained has been analyzed by X-ray diffraction and identified as consisting of CAU-1-$N_3$ crystallized hybrid solid: the diffractogram that is implemented on the CAU-1-$N_3$ solid is the one that is provided by FIG. 1. The analysis that is implemented on the CAU-1-$N_3$ crystallized hybrid solid by XRD demonstrates that the post-modification treatment that makes it possible to replace the —$NH_2$ amino group by the —$N_3$ azide group does not affect the structure and the crystallinity of the solid.

The FT-IR analysis reveals the presence of the —$N_3$ azide group on each of the deprotonated terephthalate ligands in the CAU-1-$N_3$ solid. The spectrum that is obtained by FT-IR has a characteristic band of the azide group at 2,124 $cm^{-1}$. The bands at 3,454 and 3,386 $cm^{-1}$ that correspond to the —$NH_2$ group have disappeared.

The $^1$H-NMR analysis is implemented on a sample of the CAU-1-$N_3$ hybrid solid, after digestion and total dissolution of the sample in a DCl/$D_2O$/DMSO-$d_6$ deuterated mixture according to an operating mode that is described in the literature (Z. Q. Wang, S. M. Cohen, *Journal of the American Chemical Society,* 2007, 129, 12368-12369): 10 mg of CAU-1-$N_3$ hybrid solid is digested and dissolved in 1.5 ml of deuterated DMSO and 0.2 ml of a dilute DCl solution (prepared from a solution that contains 0.23 ml of DCl/$D_2O$ at 35% and 1 ml of deuterated DMSO).

Coupled to the FT-IR analysis, the $^1$H-NMR analysis confirms the presence of the $N_3$ azide group in the aromatic cycle of the deprotonated terephthalic ligand. $^1$H NMR, 250 MHz, t.a, δ (ppm/(DCl/$D_2O$/DMSO-$d_6$)): δ=7.73-7.83 ppm, m, 3H, ArH. The 3 protons that lead to the detection of the multiplet correspond to 3 protons that are carried by the aromatic cycle of the 2-azido-terephthalate ($N_3$-bdc) ligand.

The comparison of the IR and $^1$H-NMR spectra that are obtained for the CAU-1 solid and for the CAU-1-$N_3$ solid demonstrates the effectiveness of said post-modification treatment—with the comparison of $^1$H-NMR spectra obtained for the CAU-1 solid and for the CAU-1-$N_3$ solid making it possible to estimate at 98% the rate of modification of the amino groups into $N_3$ azide groups—by quantifying the decrease of the relative area of the signals of the CAU-1 compound relative to those of the CAU-1-$N_3$ compound.

The invention claimed is:

1. A CAU-1-$N_3$ crystallized hybrid solid with an organic-inorganic matrix, of a three-dimensional structure, containing an inorganic network of aluminum-based metal centers that are connected to one another by $N_3$-bdc organic ligands, whereby said solid has an X-ray diffraction diagram that includes at least the lines that are recorded in the table below:

| 2 Theta (°) | $d_{hkl}$ (Å) | $I/I_o$ |
|---|---|---|
| 6.93 | 12.74 | FF |
| 9.68 | 9.13 | Ff |
| 9.98 | 8.85 | F |
| 11.94 | 7.41 | F |
| 13.92 | 6.36 | Ff |
| 15.37 | 5.76 | Ff |
| 15.76 | 5.62 | Ff |
| 16.97 | 5.22 | Ff |
| 18.30 | 4.84 | Ff |
| 19.41 | 4.57 | Ff |
| 20.03 | 4.43 | Ff |
| 20.64 | 4.30 | Ff |
| 21.19 | 4.19 | Ff |
| 22.30 | 3.98 | Ff |
| 23.02 | 3.86 | Ff |
| 23.95 | 3.71 | Ff |
| 24.34 | 3.65 | Ff |
| 24.84 | 3.58 | Ff |
| 25.57 | 3.48 | Ff |
| 26.78 | 3.33 | Ff |
| 27.41 | 3.25 | Ff |
| 28.70 | 3.11 | Ff |
| 29.11 | 3.06 | Ff |
| 29.38 | 3.04 | Ff |
| 30.30 | 2.95 | Ff |
| 30.98 | 2.88 | Ff |
| 31.81 | 2.81 | Ff |
| 32.08 | 2.79 | Ff |
| 32.52 | 2.75 | ff |
| 33.23 | 2.69 | ff |
| 34.69 | 2.58 | ff |
| 35.01 | 2.56 | ff |
| 36.15 | 2.48 | ff |
| 37.04 | 2.42 | ff |
| 37.54 | 2.39 | ff |
| 38.50 | 2.34 | ff |
| 38.73 | 2.32 | ff |
| 39.42 | 2.28 | ff |
| 39.98 | 2.25 | ff |
| 40.93 | 2.20 | ff |
| 41.89 | 2.16 | ff |
| 42.49 | 2.13 | ff |
| 43.54 | 2.08 | ff |
| 44.56 | 2.03 | ff |
| 44.77 | 2.02 | ff |
| 46.00 | 1.97 | ff |
| 46.34 | 1.96 | ff |
| 47.15 | 1.93 | ff |
| 47.42 | 1.92 | ff |

-continued

| 2 Theta (°) | $d_{hkl}$ (Å) | $I/I_o$ |
|---|---|---|
| 48.29 | 1.88 | ff |
| 49.26 | 1.85 | ff |
| 50.10 | 1.82 | ff |
| 50.32 | 1.81 | ff |
| 51.41 | 1.78 | ff |
| 51.87 | 1.76 | ff | where
FF = Very High;
F = High;
m = Medium;
mf = Medium Low;
f = Low; and
ff = Very Low, with the relative intensity $I/I_o$ being provided in relation to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85.

2. The CAU-1-$N_3$ crystallized hybrid solid according to claim 1, having a crystalline structure that is identical to the one of the CAU-1 crystallized hybrid solid.

3. The CAU-1-$N_3$ crystallized hybrid solid according to claim 1, wherein said three-dimensional structure has wheel-shaped bricks of $[Al_8(OH)_4(OCH_3)_8]^{12+}$ that are linked to one another by 12 deprotonated terephthalic ligands ($-O_2C-C_6H_3(N_3)CO_2-$).

4. The CAU-1-$N_3$ crystallized hybrid solid according to claim 1, such that it has a chemical composition that has $Al_4(OH)_2(OCH_3)_4(N_3\text{-bdc})_3$ for a base pattern.

5. The CAU-1-$N_3$ crystallized hybrid solid according to claim 4, such that each aluminum atom is surrounded by three oxygen atoms of three deprotonated terephthalic ligands $N_3$-bdc, an oxygen atom from hydroxyl groups, and two oxygen atoms from methoxyl groups.

6. A process for the preparation of a CAU-1-$N_3$ crystallized hybrid solid according to claim 1, starting from a CAU-1 crystallized hybrid solid, wherein the process comprises at least the following:

i/ introducing, into a polar solvent S, of said CAU-1 crystallized hybrid solid, an organic compound Q that contains an $N_3$ azide group, and is trimethylsilyl azide (TMS-$N_3$), triflyl azide (Tf$N_3$), p-tosyl azide (Ts$N_3$), or sodium azide (Na$N_3$) and an intermediate reagent R that contains an $NO_2$ nitrite group, and is tert-butyl nitrate, in a proportion such that the reaction mixture has the following molar composition, based on a molar equivalent of the $-NH_2$ group that is present in the CAU-1 solid:

1CAU-1:1-40R:1-30Q:100-400S ii/ reacting of said reaction mixture at a temperature of between 0 and 100° C. for a period of between 1 and 24 hours to obtain said CAU-1-$N_3$ crystallized hybrid solid, iii/ filtering and washing of said CAU-1-$N_3$ crystallized hybrid solid, iv/ drying said CAU-1-$N_3$ crystallized hybrid solid.

7. The process for preparation according to claim 6, wherein said CAU-1 crystallized hybrid solid is dried in advance before being introduced into said polar solvent.

8. The process for preparation according to claim 6, wherein said polar solvent S is selected from among tetrahydrofuran (THF) and acetonitrile.

9. The process for preparation according to claim 6, wherein said reaction mixture has the following molar composition, based on a molar equivalent of the $-NH_2$ group that is present in the CAU-1 solid:

1CAU-1:10-30R:10-20Q:100-200S.

10. The process for preparation according to claim 6, wherein ii) is implemented at ambient temperature.

11. The process for preparation according to claim 6, wherein ii) is conducted for between 5 and 15 hours.

* * * * *